(12) United States Patent
Barger et al.

(10) Patent No.: US 8,220,985 B2
(45) Date of Patent: Jul. 17, 2012

(54) RETRACTABLE PIN MIXING SAMPLE FORMING DEVICE

(75) Inventors: Mark Alan Barger, Midland, MI (US); Parvinder Singh Walia, Midland, MI (US); Matthew T. Bishop, Midland, MI (US); Anthony Charles Neubauer, Piscataway, NJ (US); Joseph Dooley, Midland, MI (US); Shih-Yaw Lai, Pearland, TX (US); Luciana Rudolph, Herseburg, GA (US)

(73) Assignee: Dow Global Technologies LLC, Midland, MI (US)

( * ) Notice: Subject to any disclaimer, the term of this patent is extended or adjusted under 35 U.S.C. 154(b) by 824 days.

(21) Appl. No.: 12/278,311

(22) PCT Filed: Feb. 7, 2007

(86) PCT No.: PCT/US2007/003290
§ 371 (c)(1),
(2), (4) Date: Jan. 23, 2009

(87) PCT Pub. No.: WO2007/095036
PCT Pub. Date: Aug. 23, 2007

(65) Prior Publication Data
US 2009/0316520 A1 Dec. 24, 2009

Related U.S. Application Data

(60) Provisional application No. 60/772,006, filed on Feb. 10, 2006.

(51) Int. Cl.
*B01F 11/00* (2006.01)
(52) U.S. Cl. ........ 366/257; 366/193; 366/268; 366/332; 222/246; 604/89

(58) Field of Classification Search .................. 366/129, 366/130, 140, 193, 256, 257, 268, 269, 332, 366/337, 194–196, 189; 206/221, 219; 604/89; 222/246
See application file for complete search history.

(56) References Cited

U.S. PATENT DOCUMENTS
1,612,996 A * 1/1927 Waagbo ......................... 222/252
(Continued)

FOREIGN PATENT DOCUMENTS
EP 0188981 7/1986
(Continued)

OTHER PUBLICATIONS

Forest et al., "Monodomain response of arbitrary aspect ratio nematic polymers in general linear planar flows", Journal of Non-Newtonian Fluid Mechanics, 2004, pp. 17-31, vol. 118, Elsevier B.V.
(Continued)

*Primary Examiner* — Yogendra Gupta
*Assistant Examiner* — Emmanuel S Luk

(57) ABSTRACT

The invention is a device for processing materials comprising a mixing chamber having a valve for removal of the material from the mixing chamber and a piston which fits within the mixing chamber in a manner such that the piston can be moved to remove substantially all material from the mixing chamber via the valve; at least one, preferably at least two, retractable mixing element(s) wherein each of such elements is movable in and out of the mixing chamber through a port wherein the element and port are configured such that during mixing and when the element is withdrawn from the mixing chamber substantially no material is removed from the mixing chamber via the port. The invention is also a method of using such a device and a system comprising use of such devices in an automated or partially automated array.

10 Claims, 3 Drawing Sheets

U.S. PATENT DOCUMENTS

| | | | | |
|---|---|---|---|---|
| 3,373,906 | A * | 3/1968 | De Hart et al. | 222/235 |
| 3,724,077 | A | 4/1973 | Preston et al. | |
| 3,789,670 | A * | 2/1974 | Rosenwald | 73/864.62 |
| 4,116,240 | A * | 9/1978 | Guiney | 604/89 |
| 4,277,184 | A * | 7/1981 | Solomon | 366/139 |
| 4,440,500 | A * | 4/1984 | Schneider | 366/162.5 |
| 4,459,865 | A * | 7/1984 | Welker | 73/864.62 |
| 4,464,056 | A * | 8/1984 | Schmitz et al. | 366/134 |
| 4,490,048 | A * | 12/1984 | Schlueter | 366/134 |
| 4,510,120 | A * | 4/1985 | Bauer | 422/133 |
| 4,773,564 | A * | 9/1988 | Wallner | 222/145.6 |
| 5,071,040 | A * | 12/1991 | Laptewicz, Jr. | 222/235 |
| 5,352,036 | A * | 10/1994 | Haber et al. | 366/130 |
| 5,630,800 | A * | 5/1997 | Blank et al. | 604/82 |
| 5,971,953 | A * | 10/1999 | Bachynsky | 604/90 |
| 6,536,936 | B1 * | 3/2003 | Bellasalma et al. | 366/138 |
| 6,544,233 | B1 * | 4/2003 | Fukui et al. | 604/191 |
| 6,550,957 | B2 * | 4/2003 | Mizutani et al. | 366/189 |
| 6,736,537 | B2 * | 5/2004 | Coffeen et al. | 366/130 |
| 6,770,340 | B2 | 8/2004 | Zumbrunnen et al. | |
| 6,866,653 | B2 * | 3/2005 | Bae | 604/191 |
| 7,018,089 | B2 | 3/2006 | Wenz et al. | |
| 2004/0145077 | A1 | 7/2004 | Fleischer et al. | |
| 2005/0179156 | A1 | 8/2005 | Carlson et al. | |
| 2006/0227653 | A1 | 10/2006 | Keller | |
| 2006/0273109 | A1 | 12/2006 | Keller | |
| 2007/0041267 | A1 * | 2/2007 | Coffeen et al. | 366/189 |

FOREIGN PATENT DOCUMENTS

| | | |
|---|---|---|
| GB | 1214053 | 12/1970 |

OTHER PUBLICATIONS

Fuller et al., "Flow Birefringence of Concentrated Polymer Solutions in Two-Dimensional Flows", Journal of Polymer Science: Polymer Physics Edition, 1981, pp. 557-887, vol. 19, John Wiley & Sons, Inc.

Gilman et al., "Development of High Throughput Methods for Polymer Nanocomposite Research", Fire Retardant Chemicals Association, Fall Conference Proceedings, 2002, pp. 27-45.

Jana et al., "Experimental and Computational Studies of Mixing in Complex Stokes Flows: The Vortex Mixing Flow and Multicellular Cavity Flows", J. Fluid Mech, 1994, vol. 269, pp. 199-246, Cambridge University Press.

Malhotra, "Combinatorial Materials Development: Chapter 1 Combinatorial Chemistry of Materials, Polymers, and Catalysts", ACS Symposium Series, 2002, vol. 814, pp. 1-21, American Chemical Society.

Meredith et al., "Combinatorial Methods for Investigations in Polymer Materials Science", MRS Bulletin, 2002, pp. 330-335, www.mrs.org/publications/bulletin.

Meredith et al., "High-Throughput Measurement of Polymer Blend Phase Behavior", Macromolecules, 2000, pp. 5760-5762, vol. 33, American Chemical Society.

Nyden et al., "Development of a Continuous Flow Flame Test Extruder for High-Throughput Formulation and Screening of Flame Retardants and More Fire Resistant Materials", Fire Retardant Chemicals Association, Spring Conference Proceedings, 2000, pp. 1-5.

Tadmor et al., "Introduction to Polymer Processing" and "Mixing", Principles of Polymer Processing, 1979, Ch. 1 and 11, pp. 1-27 and 404-466, John Wiley & Sons, Inc.

Wroczynski et al., "High-Throughput Methods for Evaluation of Process Degradation of Polymer Formulations", Proceedings ANTEC-SPE, 2003, pp. 2679-2683.

Zumbrunnen et al., "Chaotic Mixing as a Means to Develop Nano-Scale Structures in Polymeric Materials", ANTEC 2002, 5 Pages.

Zumbrunnen et al., "Novel sub-micron highly multi-layered polymer films formed by continuous flow chaotic mixing", Chemical Engineering Science, 2001, pp. 3893-3897, vol. 56, Issue 12, Elsevier Science Ltd.

* cited by examiner

RETRACTABLE PIN MIXING SAMPLE FORMING DEVICE

CROSS REFERENCE TO RELATED APPLICATIONS

This application is a §371 filing from PCT International Patent Application number PCT/US07/003,290 filed Feb. 7, 2007, and claims priority from U.S. Provisional patent application No. 60/772,006, filed Feb. 10, 2006, which are both incorporated herein by reference in their entireties.

FIELD OF THE INVENTION

This invention relates to a device for and method of mixing materials.

BACKGROUND OF THE INVENTION

High throughput screening methodologies are useful for rapid assessments of many material combinations. While US Patent Publication 2005/0179156 sets forth various sample formation techniques that can be used in high throughput screening, there is still a need for a system that has improved throughput.

While pin or rod mixers are known, e.g., see Tadmor & Gogos, Principles of Polymer Processing, Ch. 1, 11; Chris Rauwendaal, Polymer Mixing; Zumbrunnen & Inamdar, Chem. Eng. Sci., 56 (2001), 3893, the existing form of these mixers generally has not been suitable for use in high throughput research techniques.

As used herein, "workflow" refers to an integrated process comprised of at least the following steps: experimental design, blending, transformation into test specimens, testing to determine one or more properties relevant to the research or development problem at hand, and data analysis. In this context, "high throughput" refers to a workflow where these steps are very well integrated and time-compressed such that the overall time to execute the workflow per material is anywhere from 2 to 100 or more times as fast as a standard non-high throughput workflow.

SUMMARY OF THE INVENTION

The present invention is a device well-suited and enabling for high throughput sample preparation of various compositions These compositions preferably are selected from the group that includes but is not limited to polymeric or oligomeric based compositions (e.g., blending of two polymers or oligomers, reactive blending to form polymers or oligomers or alter their molecular structure, forming a composite material of a non-polymeric component in a polymer or oligomer), slurries, and other materials that require mixing or blending.

The present invention in its Various embodiments provides all or some of the following benefits: it is mechanically and operationally simple and robust; it is substantially self-cleaning in operation; it facilitates the recovery of substantially all of the material thereby providing high yields; it can be made at a variety of scales; it allows the sample size to be varied for a given device; it is well-suited for automation, robotics, and parallelization; it provides short sample preparation cycle-times, high yields; it has flexibility in materials that can be prepared; and it has flexibility in the form of the final sample.

Thus according to a first embodiment the invention is a device for processing a material comprising:

a mixing chamber having a valve for removal (i.e., exit valve) of the material from the mixing chamber and a piston which fits within the mixing chamber in a manner such that the piston can be moved to remove substantially all material from the mixing chamber via the valve;

at least one, preferably at least two, retractable mixing element(s) wherein each of such elements is movable in and out of the mixing chamber through a port wherein the element and port are configured such that during mixing and when the element is withdrawn from the mixing chamber substantially no material is removed from the mixing chamber via the port.

According to a second embodiment the invention is a method of preparing a sample comprising a) providing a material to be prepared into a sample, the material preferably comprising at least two components, b) introducing the material to the mixing chamber of the device described above, c) mixing the material by movement of the mixing elements, d) withdrawing the mixing elements from the mixing chamber e) removing the material from the mixing chamber via the valve by compression of the material with the piston. Preferably, in the removing step the material is injected into a mold of the shape desired or extruded through a die into the desired shape for subsequent testing of the sample, e.g., determination of mechanical properties, thermal properties, rheological properties, optical properties, etc.

According to a third embodiment the invention is a system comprising at least two, preferably at least three, more preferably at least four of the above devices arranged in an array and connected to a control device. The control device allows automation of at least one of the steps of loading the chamber, mixing, and removing the sample from the chamber.

According to a fourth embodiment the invention is a method of using the system to form samples as part of a complete high throughput material testing workflow.

DETAILED DESCRIPTION OF THE INVENTION

Figure 1:
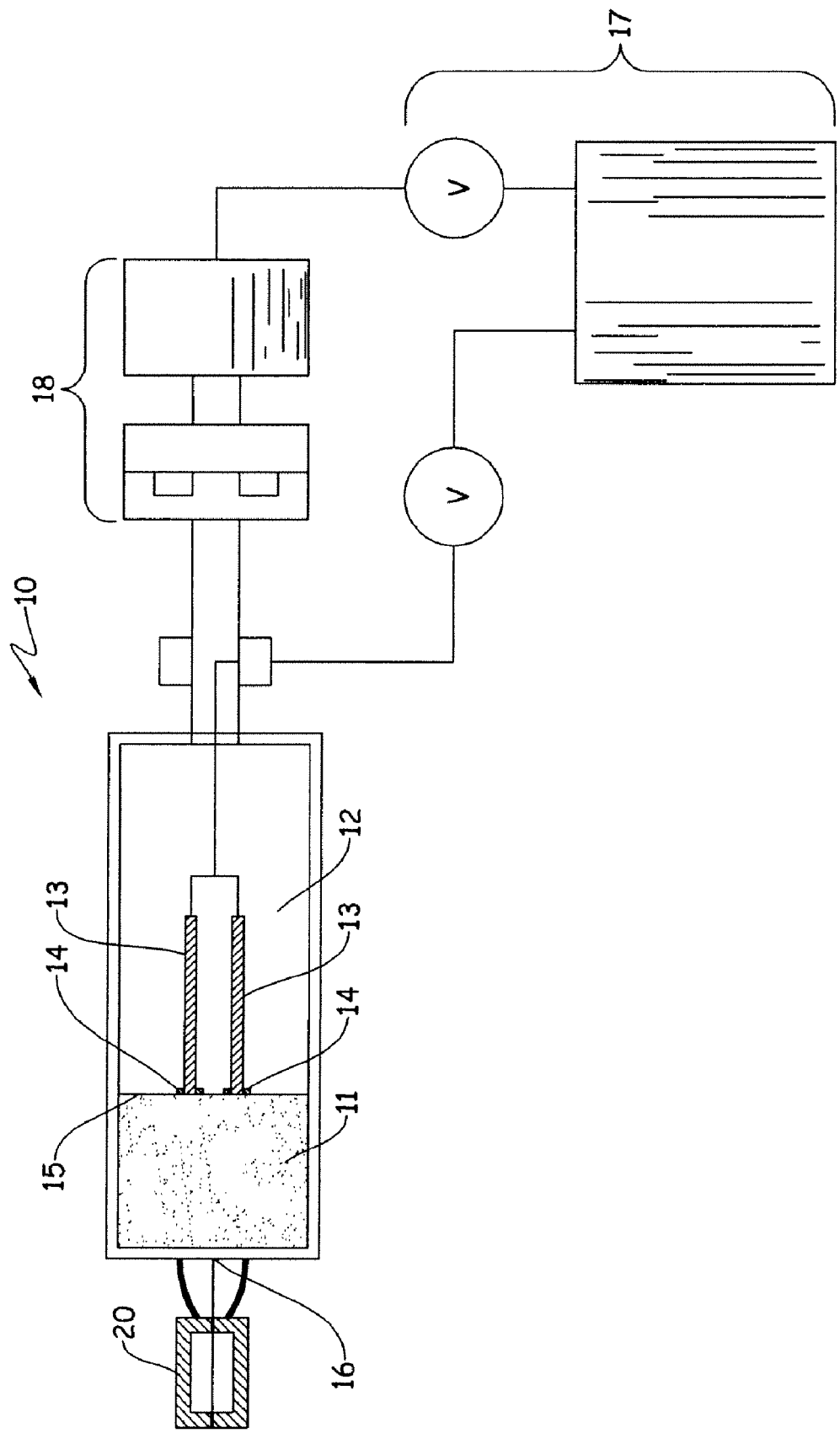
FIG. 1 is an illustration of one possible embodiment of the device with mixing elements retracted.

The mixing chamber and piston are preferably of a size and shape that makes the device simple, durable, and suitable for high throughput workflows. Thus, referring to FIGS. 1-3, one example of a device within the scope of the invention is shown having the mixing chamber 11, the piston 12, and the mixing elements 13. In this embodiment, the mixing elements 13 are shown as being inserted through ports 14 in the face 15 of the piston 12 that forms one side of the mixing chamber 11. However, mixing elements 13 could reasonably be located alternatively or additionally on the sides or opposite wall of the mixing chamber 11. The valve 16 is shown in its preferred location opposite the piston 12 but other locations could be used if desired. The term valve is used herein in the broadest possible context to mean a structure that stops or prevents flow of material but can be moved manually or automatically to allow flow of material. This particular embodiment shows a pneumatic or hydraulic control system 17 for engaging the mixing elements 13 and/or the piston 12 and a motor 18 for rotating the piston 12 thereby causing movement of the mixing elements 13.

Figure 2:
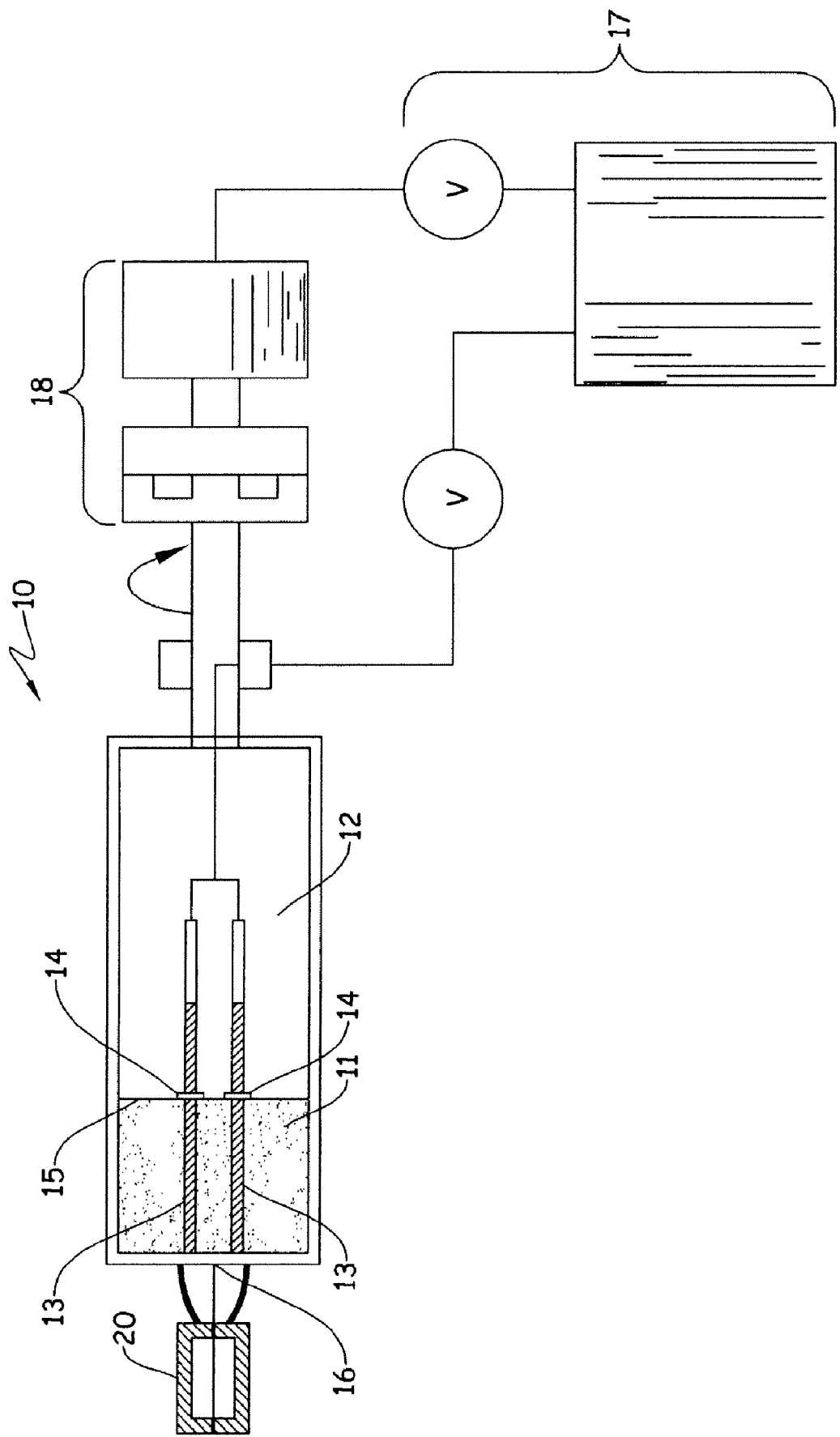
FIG. 2 is an illustration of one possible embodiment of the device with mixing elements engaged.
Figure 3:
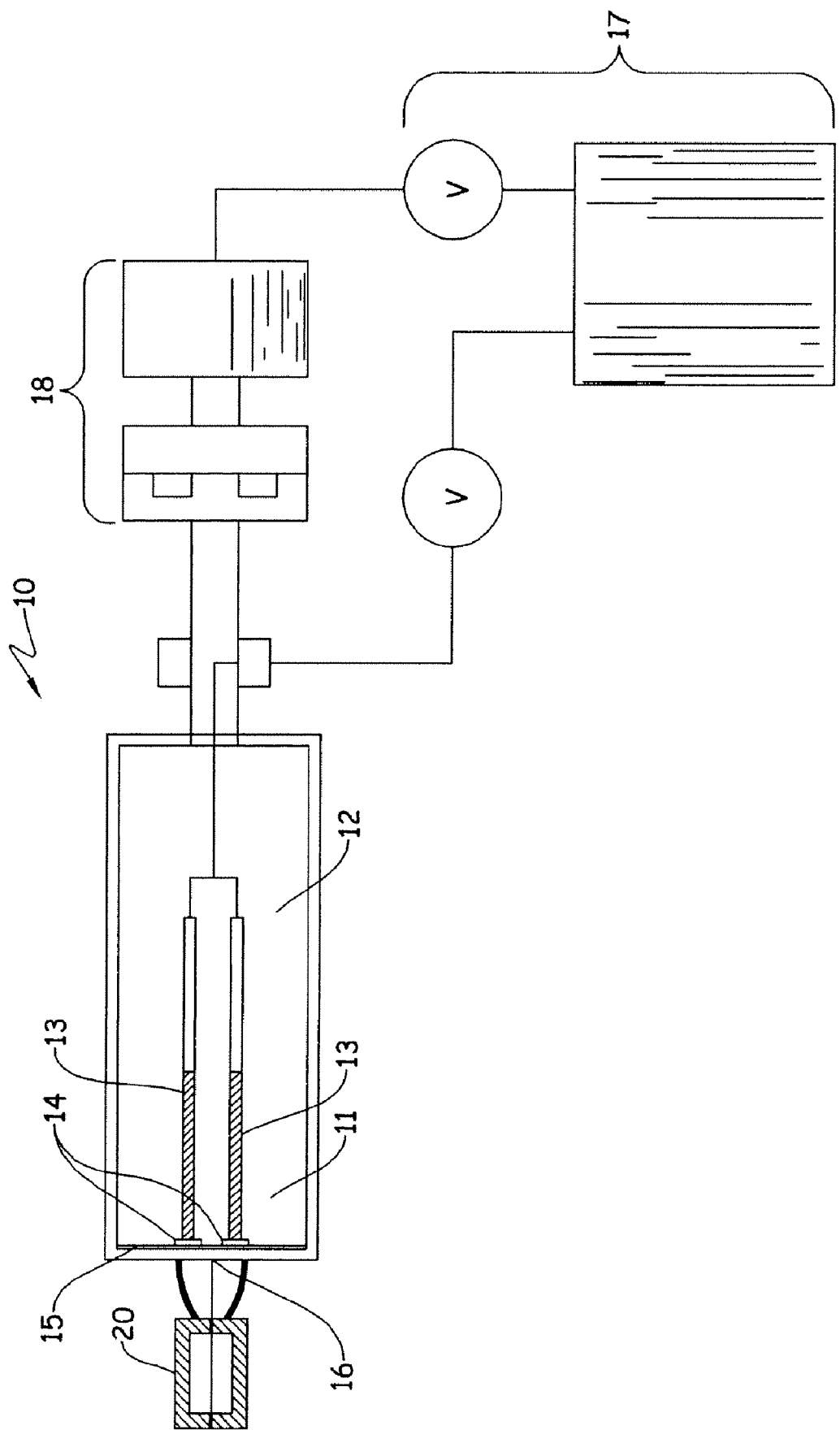
FIG. 3 is an illustration of one possible embodiment of the device upon removal of material from the mixing chamber.

In FIG. 3, the valve 16 is shown as injecting the sample into a mold 20 for formation of the desired sample shape after mixing. FIG. 1 shows the device 10 with piston 12 and mixing elements 13 withdrawn. FIG. 2 shows the device 10 with mixing elements inserted into the mixing chamber 11.

Mixing can occur by movement of the mixing elements, e.g., rotation (note that the preferably the element itself may rotate on its axis, or as shown in the figures, the piston could rotate causing the mixing elements to move in the chamber), oscillation in and out, or some combination of such movements. The mixing elements may be moved in various modes of operation such as steady state or time periodic, e.g., chaotic motion or time variant, etc. These modes and sequences of pin rotation and oscillations can be combined in any desired manner, along with variations in rotation directions and speeds. According to one preferred embodiment the device further includes an element or means for providing ultrasonic vibration within the device. For example, ultrasonic vibration of the piston, mixing elements, exit valve, mixing chamber or extrusion die or mold attached to the device. This would involve vibration of the material being processed by the vibration of the piston, mixing elements or exit valve in the direction of the primary axis. The frequency, amplitude and intensity of vibration may be controlled by the control system provided for the device.

According to one embodiment, therefore, the device comprises a mixing chamber having a primary axis and a uniform cross section along the primary axis; a piston movable along the primary axis of the mixing chamber and having a cross section of the same shape and substantially the same size as the cross section of the mixing chamber; at least one retractable mixing element which has a length and a cross section which is uniform along the length of the mixing element, which element is movable in and out of the mixing chamber through a port having a cross section of the same shape and substantially the same size as the cross section of the mixing element, and a valve, preferably, on an opposite wall of the mixing chamber from the piston.

Preferably, there are at least two mixing elements and more preferably at least four mixing elements. The mixing elements may be of various shapes in cross section, e.g., circular, oval, square, triangular, star shaped, vaned or fluted rods, etc. According to one embodiment the mixing element has a length and a cross section which is uniform along the length of the mixing element and the port has substantially the same cross section and size to avoid inadvertent removal of the material from the mixing chamber via the port when the mixing element is withdrawn. Alternatively, screw symmetry in a mixing element could be used as that would also promote mixing in additional directions within the chamber. A single off center mixing pin could be used to promote dispersive mixing. The mixing elements could also be inserted at various angles to accommodate the desired mixing effect. The mixing elements may be inserted from opposite sides of the mixing chamber. This enables some variation in the spacing between the mixing elements. The port should seal snugly around the mixing element to minimize leakage of material but must allow for movement of the mixing element in and out of the mixing chamber. A seal or gasket may be used at the port to prevent leakage of the material. This seal or gasket should be made from materials that are inert to the materials to be processed.

The mixing elements may be made of materials that would be substantially inert to the materials being mixed. The elements need not be entirely rigid but should be sufficiently rigid to effectively mix the material. Examples of potentially suitable materials include metals, ceramics and polymeric materials. The inventors have discovered that use of four rod-like mixing elements in a rotational method substantially improves mixing and decreases mixing time as compared to a device with only two rod-like mixing elements used in similar fashion. The mixing elements may be used by rotation, oscillation, and other appropriate movement. The movement of the mixing elements may be imparted by use of stepper motors or other types of motors.

The size of the mixing chamber is preferably small for use in high throughput workflows—accommodating up to about 100 cm$^3$, more preferably up to 50 cm$^3$, more preferably still up to 20 cm$^3$, yet more preferably up to about 10 cm$^3$ (approximately 10 g) of material. The mixing chamber preferably handles samples as small as about 0.5 cm$^3$, more preferably the samples are at least about 1 cm$^3$ (i.e., approximately 1 g). The shape of the mixing chamber is not critical provided the piston can adequately remove substantially all the material from the chamber and the mixing elements can be effectively extended and retracted from the mixing chamber. By varying the displacement of the piston, samples of various sizes can be mixed in the same chamber effectively. For example, for a 5 g sample a mixing chamber designed with a maximum capacity of about 10 g, the piston would be partially engaged to make the mixing chamber effectively smaller. A substantially cylindrical mixing chamber may be preferred for simplicity. The piston can be engaged using appropriate devices that would impart linear motion to the piston—such as a pneumatic actuator, stepper motors, or the like, or by electromechanical or hydraulic means. The mixing chamber and piston are preferably formed from materials that are substantially inert to the materials to be processed. While suitable materials of construction depend on the intended usage of the device general examples include, metals, ceramics, and polymeric materials.

In mixing polymers and some other materials it may be desirable to control the temperature in the mixing chamber, thus a heating element or a cooling element may be used in or with the device or incorporated as a feature in the device. For example, heating or cooling jackets or elements around the mixing chamber may be helpful. The small scale of the preferred devices makes them particularly suitable for these types of heat transfer mechanisms.

Various sensors for monitoring the mixing chamber may also be used. For example, temperature, pressure, or spectroscopic, e.g., UV or Raman, sensors may be used.

If desired the mixing elements and/or the piston may be connected to devices to measure viscosity of the material, e.g., measurement of pressure in the chamber while expelling the material with a controlled rate of piston displacement (analogous to a capillary rheometer); torque measurements on mixing elements; or measuring the length of time required to expel all the material from the chamber under constant force piston displacement (analogous to a melt index machine). As yet another example, with mixing elements retracted from mixing chamber, torque measurement could be made with piston rotation in steady or oscillatory shear (analogous to an oscillatory rheometer). All these measurements could be used to estimate or calculate viscosity according to standard calculation methods.

The device is primarily contemplated for mixing of a relatively wide range of materials. These materials include particularly polymeric or oligomeric based compositions (e.g., blending of two polymers or oligomers, reactive blending of monomers to form polymers or oligomers, reactive mixing to alter the molecular structure of polymers or oligomers, or forming a composite material of a non-polymeric component in a polymer or oligomer), slurries, food products, pharmaceutical products, adhesives, sealants, caulks, and other materials (particularly viscous materials) that require mixing or blending. The device is particularly useful for melt blending of various polymers or for incorporation of additives and fillers into polymeric materials. The non-polymeric components to be blended into polymers could include solids, liquids, and gases. The non-polymeric components are typically the minor phase (preferably less than 50%, more preferably less than 25% by weight of the composition) of the composition. The non-polymeric components would be any that are desired to be used in combination with the polymer such as fillers, nanoparticles, fire retardant additives, flow control agents, plasticizers, stabilizers, colorants, blowing agents, impact modifiers, slip agents, wetting agents, surface lubricity modifiers, or other materials useful in polymeric materials or polymeric composites.

The device may also potentially be used as a small scale reactor to carry out polymerization or advancement, e.g., to make thermoplastic polyurethanes or urethane or epoxy prepolymers. It could also be used to carry out other reactive processing such as grafting, branching, crosslinking or vulcanization, functionalization, neutralization, compatibilization or chain scission of polymers. Materials may be added to the device in solid, liquid, or gaseous form and the time of addition may also vary depending on the nature of the reactive process being carried out. Use of torque measurements on the mixing elements to monitor the reaction in-situ would be particularly helpful when the device is used for reactive processing. Alternatively the sensors or probes discussed above can be used in the mixing chamber to measure the state of mixing or the extent of reaction.

Additional components may be introduced into the mixing chamber during the course of mixing and/or reaction via input ports. Thus, according to one preferred embodiment the chamber can be designed to have one or more input ports, or the valve can be used for filling the chamber. Alternatively, the chamber could be of a clam shell or similar design such that it can be completely opened for charging with material and/or cleaning.

As noted a mold can be connected at the outlet or valve to immediately form the mixed material into a desired shape for subsequent processing, testing, or use. The outlet is desirably set up such that various molds of different shapes can be attached. The shape will be determined by the subsequent processing, testing, or use. For example, if it is desired to perform tensile tests on the sample a suitable mold to produce samples for tensile testing may be used. Alternatively, the sample can be extruded in the desired form (films, fibers, profiles) with the attachment of an appropriately shaped die on the exit port.

Because the primary motions in the device are preferably linear (e.g., piston movement and extension and retraction of mixing elements) or rotational, the device is well suited for automation. Computer control of the various motors, actuators, valves, sensors, and other auxiliary devices (e.g., for material loading) to provide control of the overall process is preferable. Computer control provides benefits of labor-saving and improved reproducibility of the process. Automation and computer control of the device and process is preferably also integrated with automation and control of initial material loading and any subsequent material additions into the device.

The devices can be used in combination with like devices in an array. The array may be any suitable configuration including, for example, a linear array operated in series (slaved to common drives) or parallel (independently controlled); a grid array (e.g., where each row is operated in series or parallel or where all devices are operated in parallel); or a rotary carousel arrangement. A rotary carousel arrangement may preferably involve stations for different operations such as loading, melting, mixing, and molding. Use of the automated devices in an array arrangement, preferably with additional control for sequencing of operations among the several devices in the array, facilitates use of the device in high throughput workflow situations, especially high throughput workflows which require melt blending of polymeric materials and transformation into a form suitable for testing, e.g., as the front end of a complete high throughput material testing workflow.

Mechanical actuation can be accomplished by known approaches such as pneumatic, hydraulic, or electrical means (or some combination of the three). Actuation by hydraulic (using servo motors and ball screws) or electrical means is preferable for higher viscosity polymers or compounds. Hydraulic or electromechanical actuation of the piston is preferred for the purpose of obtaining more rapid dispensing of the mixed material into a mold (i.e., to more nearly simulate a true injection molding operation). A preferred embodiment may take the form of a rotary carousel setup with multiple banks where each bank is used for completing individual steps, e.g., (1) robotic sample loading in mixing chamber (2) melting and compaction by extending piston into chamber (3) mixing using appropriate number of pins and sequence of rotations (4) material transformation into dimensioned sample via use of mold or die (5) robotic dispensing of fabricated sample. Pulsed steam heating/water cooling may be used to rapidly and controllably thermostat the mold and enable reduced cycle time. Alternatively, multiple molds may be shuttled into place to allow for parallel processing (one samples being molded while another is being cooled and de-molded). Molds could be clamped via mechanical or magnetic means. Specific designs and strategies may be employed for mold manipulation to allow for rapid and automated mold opening and subsequent sample removal.

Preferably the cycle time for loading mixing and discharge is less than 30 minute, more preferably less than 10 minute.

Preferably the yield from the device is greater than about 95% based on charge of material to the device, and more preferably greater than 98%.

EXAMPLES

A device with a cylindrical piston-cylinder design and two retractable mixing pins was built. In this device, the mixing pins are located opposite from the piston. Two stepper motors connected to the mixing pins through two flexible connecting rods are used to cause rotation of each pin around its axis. Material is charged into the mixing chamber when the piston is fully retracted which leaves an opening at the top of the mixing chamber. The piston moves axially downward to compact the material as it melts and consolidates. The mixing chamber and any extrusion dies are electrically heated. A needle valve controls material flow out of the chamber. Pneumatic cylinders control axial movement of the piston, with a 15-fold pressure amplification over the source air. A tape die can be attached at the exit to shape the extrudate into nominal 2.5 cm wide by 1 mm thick strips. Alternatively, a mold can be attached at the exit. Software on a laptop computer is used to command the stepper motor controller to control the rotation of the mixing pins according to the prescribed mixing protocol (as described below). The operation of this device was manual with regards to material loading, valve actuation, and material collection or extraction from the mold or die. Automation of these basic functions could easily be incorporated in future design iterations.

A general method for operating the device is as follows:
1. Preheat the machine to the desired temperature.
2. Charge material into the open chamber.
3. Soak time for degassing (1 minute to 3 minute) and melting.
4. Extend piston into the chamber.
5. Compact sample, gradually ramping pressure and allowing sample to fully melt.
6. Extend mixing pins into the chamber.
7. Begin time periodic motion of the mixing pins.
8. Stop and retract pins.
9. Open needle valve.
10. Extend piston downward to inject material out of the device and into a mold or a die.
11. Retract piston and prepare for next sample.

In operation, this mixing device was mechanically robust and there was no observed leakage around either the piston or the mixing pins, and these components could be easily translated axially using pneumatic pressure. The device was essentially self-cleaning with material yield greater than 99% when the piston-chamber clearances were low (0.0005 inch (0.0127 mm) to 0.0010 inch (0.0254 mm)).

Example 1

Using the above device, a simple square wave time periodic motion was employed for the preparation of blends of polystyrene and poly(methyl methacrylate). A mixing period consisted of a set number of revolutions of one pin at constant speed followed by the same number of revolutions of the second pin. For this mixing program, the motion of the two pins was out-of-phase, but in this case in on/off fashion as opposed to sinusoidally varying. The overall mixing program consists of a number of periods (i.e., one on/off-off/on sequence) where it was possible to vary the constant pin rotational speed and revolutions per period.

STYRON™ 685 polystyrene (PS) (from The Dow Chemical Company) was mixed with 5% wt/wt poly(methyl methacrylate) (PMMA) from Aldrich (37003-7, nominal molecular weight=100,000 g/gmol) in the device for different times. The conditions selected for mixing were 6 pin revolutions/period and 15 rpm. The mixed material was extruded through a round die and samples were withdrawn at six equally spaced positions from the round extrudate. These samples were analyzed via infrared spectroscopy (IR) for blend composition. Spectra were acquired with Perkin Elmer Spectrum One FT-IR and the diamond Universal ATR accessory. Band intensities were measured at 1735 cm$^{-1}$ (carbonyl stretching band) for PMMA and 1601 cm$^{-1}$ (aromatic stretching band) for PS. The ratio of PMMA band to PS band intensity is an indication of blend composition. Mixing could be quantified by the time to reach a constant composition profile, as indicated by merging of the different positional compositions. These tests showed that mixing was fast and compositional homogeneity was achieved in about 4 minute.

Example 2

The mixing capability of the 2-pin prototype mixer described in Example 1 can be enhanced by the use of multiple pins. This enhanced capability was demonstrated via CFD (computational fluid dynamics) modeling described herein. The modeling conditions used were—steady state, laminar regime, viscosity of 8000 Pa-s, density of 1064 kg/m$^3$.

According to these models a 4-pin chaotic mode of operation (square wave) is twice as effective in mixing as the comparable 2-pin chaotic case. In addition, mixing with four pins operating in steady state mixing is faster than when chaotic mode of operation, square wave is used for the same device at the same rotation speed. Increasing the rotation speed at steady state further decreases required mixing time.

Example 3

The 2-pin mixing device described in Example 1 was used to prepare a series of blends whose tensile properties were then measured. The 2-pin mixing device was equipped with a two-part split aluminum mold. The mold cavity had dimensions of 2.5 inch (63.5 mm) by 2.5 (63.5 mm) by 0.064 inch (1.62 mm), and was gated through a cylindrical channel connected to the exit path of the mixer. The cavity-containing face of the mold was bolted to the mixer baseplate and thus stationary. The parting face of the mold was moveable along rails. It was bolted in place during molding, but readily moved out of the way after part solidification for removal of the plaque and sprue. Both parts of the mold had machined channels through which fluid could be circulated for temperature control of the mold.

Blends and molded plaques were prepared by the following method. The temperatures of the chamber and base plate were set to 230° C. The two halves of the plaque mold were bolted together with the mold temperature controlled to 50° C. to 60° C. with a circulating water bath. Seven (7) grams total of cryogenically ground polymer components were weighed into a vial in the desired ratio, then shaken to roughly mix the components. With the exit valve closed, the starting mixture was loaded into the mixer chamber. The piston was immediately lowered partway into the chamber to allow it to heat and expand to facilitate sealing. The polymer was allowed to melt for 90 second. Then the piston was lowered into contact with the material at low pressure, about 200 psig (1379 kPag), in order to compact and de-aerate the material. Two minutes after the material was loaded, the mixing elements were raised. Then the mixing program was run, maintaining a pressure of about 200 psig (1379 kPag) on the piston during the mixing program. For this example, the overall mixing program consisted of repetition of a basic mixing cycle which had two parts: (a) 20 revolutions at 100 rpm with co-rotating mixing elements (clockwise, looking from the top); and (b) 20 revolutions at 100 rpm with counter-rotating mixing elements. This basic mixing cycle with length of 24 second was repeated the number of times required to give the desired total mixing time; for example, 20 times to give 8 minute of mixing. At the end of the mixing program, the mixing elements were retracted from the mixing chamber and high pressure (5000 psig (34.5 MPag) to 5500 psig (37.9 MPag)) was applied to the piston. After allowing about 30 seconds for de-aeration at high pressure, the exit valve was opened to fill the mold. The time to fill the mold was about one second at this pressure, given the viscosity of the blends and exit path dimensions. Plaques with attached sprue were removed after about three to four minutes of cooling. Plaques were visually homogeneous and substantially bubble-free. For a process with 8 minutes of mixing time, the overall cycle-time from loading of the starting mixture to removal of the plaque was about 14 minute to 15 minute.

The samples prepared were blends of different linear low density polyethylenes having various melt indices and densities (Table 3-1). Examples 3a, 3b, and 3c were prepared by the above method, with an 8 minute mixing program and with mold temperature controlled to 50° C. to 60° C. Example 3d was a repeat of 3c, with tighter control of mold temperature at 50° C. Examples 3e and 3f were repeats of 3d, but with total mixing times of four and two minutes, respectively.

TABLE 3-1

| Example ID | Component | Weight fraction |
|---|---|---|
| 3a | LLDPE-1 | 0.41 |
|  | LLDPE-2 | 0.59 |
| 3b | LLDPE-3 | 0.65 |
|  | LLDPE-4 | 0.35 |
| 3c, 3d, 3e and 3f | LLDPE-5 | 0.64 |
|  | LLDPE-6 | 0.10 |
|  | LLDPE-7 | 0.26 |

Tensile break properties were determined using an electro-mechanical test frame equipped with pneumatic grips and a ten pound load cell. Tensile specimens (ASTM D1708) were cut from plaques, both parallel and perpendicular to the flow direction. Crosshead speed was 2 inch (50.8 mm) per minute, corresponding to a strain rate of about 230% per minute assuming an effective gauge length of 0.87 inch (22.1 mm).

Normalized values of the tensile break properties that were measured for Example 3a through 3f are shown in Table 3-2 (values normalized to the parallel to flow values for Example 3a). Values reported are based on engineering stress and strain at break, averages of 4 replicates. Also shown are results for a comparative Example 3g, with the same composition as Example 3c. Comparative Example 3g used the same method as 3c, except the starting material loaded into the 2-pin mixer had been thoroughly mixed previously via multiple passes on an 18 mm twin-screw extruder with a length to diameter ratio of forty. The 2-pin mixer has excellent mixing effectiveness, as evidenced by similarity of properties for Examples 3c and 3d to this comparative Example 3g.

TABLE 3-2

| | Tensile Break Properties | | | |
|---|---|---|---|---|
| | Parallel-to-flow | | Perpendicular-to-flow | |
| | Stress | Strain | Stress | Strain |
| Ex. 3a | 1.00 | 1.00 | 1.99 | 1.54 |
| Ex. 3b | 0.98 | 0.68 | 2.05 | 1.32 |
| Ex. 3c | 1.27 | 1.12 | 1.94 | 1.58 |
| Ex. 3d | 1.31 | 1.11 | 2.14 | 1.65 |
| Ex. 3e | 1.01 | 1.02 | 2.05 | 1.56 |
| Ex. 3f | 1.24 | 1.04 | 1.88 | 1.47 |
| Ex. 3g (comp) | 1.27 | 1.14 | 1.94 | 1.56 |

The time required for preparing each of these blend examples in plaque form was less than 20 minute. The time required for testing each of these blend examples was about 30 minute: 5 minute for cutting specimens and 25 minute for tensile testing. Obviously, the operations required for evaluating properties can be done in parallel with preparation of the blends and plaques thereof. Furthermore, these property evaluations can readily be automated and accelerated, e.g., testing of multiple specimens simultaneously via commercially available multi-station mechanical test frames, testing at higher strain rate, robotic sample loading systems, and so on. Taken together, the mixing device plus mechanical property testing equipment constitutes a rapid means of preparing material compositions and evaluating their mechanical properties.

What is claimed is:

1. A device for processing a material comprising
   a mixing chamber having a valve for removal of the material from the mixing chamber and a piston which fits within the mixing chamber in a manner such that the piston can be moved to remove substantially all material from the mixing chamber via the valve;
   at least four retractable mixing elements wherein such elements are movable in and out of the mixing chamber through a port wherein the elements and ports are configured such that during mixing and when the elements are withdrawn from the mixing chamber substantially no material is removed from the mixing chamber via the port, and wherein the mixing elements rotates, and wherein the mixing chamber, piston and retractable mixing elements are cylindrical and the retractable mixing elements are arranged in a rectangular, square or diamond-shaped array such that there are two diagonally opposite pairs of mixing elements and the two pairs of diagonally opposite mixing elements rotate in opposite directions.

2. The device of claim 1, wherein the retractable mixing elements rotate and oscillate within the mixing chamber.

3. The device of claim 1, further comprising an extrusion die or mold, wherein the die or mold is connected to the valve and is outside of the mixing chamber.

4. The device of claim 1, further comprising at least one additional opening through which the materials to be mixed can be placed into the mixing chamber.

5. The device of claim 1, wherein the same device can be operated at different sample volume by controlling the level of insertion of at least one of the piston and the mixing elements into the mixing chamber.

6. The device of claim 1, further comprising an element that provides ultrasonic vibration to one or more of the pistons, mixing elements, valve for removal, or mixing chamber.

7. The device of claim 1, further comprising at least one sensor to measure properties of the sample.

8. The device of claim 7 where the at least one sensor measures force applied to move the mixing elements, the pistons, or both.

9. A system where two or more devices of claim 1, are arranged in an array.

10. The device of claim 3 further comprising an element that provides ultrasonic vibration to one or more of the extrusion die or mold attached to the device.

* * * * *